(12) United States Patent
Chen et al.

(10) Patent No.: US 11,903,708 B2
(45) Date of Patent: Feb. 20, 2024

(54) SWITCHABLE LOW VOLTAGE ELECTROCHEMICAL SENSING FOR INTERFERING SPECIES REJECTION

(71) Applicant: CALIFORNIA INSTITUTE OF TECHNOLOGY, Pasadena, CA (US)

(72) Inventors: Samson Chen, Pasadena, CA (US); Axel Scherer, Barnard, VT (US); Muhammad Musab Jilani, Pasadena, CA (US); Xiomara L. Madero, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1437 days.

(21) Appl. No.: 16/144,174

(22) Filed: Sep. 27, 2018

(65) Prior Publication Data

US 2019/0090797 A1   Mar. 28, 2019

Related U.S. Application Data

(60) Provisional application No. 62/564,921, filed on Sep. 28, 2017.

(51) Int. Cl.
*A61B 5/1486* (2006.01)
*A61B 5/1459* (2006.01)
(Continued)

(52) U.S. Cl.
CPC ........ *A61B 5/14865* (2013.01); *A61B 5/1459* (2013.01); *A61B 5/14532* (2013.01); *G01N 27/30* (2013.01); *G01N 27/419* (2013.01)

(58) Field of Classification Search
CPC .... G01N 27/419; G01N 27/30; A61B 5/1459; A61B 5/14532; A61B 5/14865; A61B 5/1486
See application file for complete search history.

(56) References Cited

U.S. PATENT DOCUMENTS

| 2003/0032874 A1* | 2/2003 | Rhodes | A61B 5/14865 600/347 |
| 2005/0161346 A1* | 7/2005 | Simpson | A61B 5/14532 205/792 |

(Continued)

FOREIGN PATENT DOCUMENTS

EP    3078965 A1   10/2016

OTHER PUBLICATIONS

International Search Report for International Application No. PCT/US2018/053068 filed on Sep. 21, 2018 on behalf of California Institute of Technology, dated Jan. 18, 2019. 3 pages.

(Continued)

*Primary Examiner* — Eric J Messersmith
(74) *Attorney, Agent, or Firm* — Steinfl+Bruno LLP

(57) ABSTRACT

A sensor implanted in tissues and including a sensing enzyme takes an electrical measurement and compares it to reference curves for the voltage current relationship. The sensor determines whether molecular compounds are present which interfere with the detection of the molecule of interest. If interfering species are found, the measurement voltage is set in a low range to reduce errors, while if the interfering species are not found, the measurement voltage is set in a high range to increase the detected signal.

19 Claims, 2 Drawing Sheets

(51) Int. Cl.
G01N 27/419 (2006.01)
G01N 27/30 (2006.01)
A61B 5/145 (2006.01)

(56) References Cited

U.S. PATENT DOCUMENTS

| | | | |
|---|---|---|---|
| 2009/0000947 A1* | 1/2009 | Akahori | C12Q 1/001 |
| | | | 204/403.14 |
| 2010/0025238 A1 | 2/2010 | Gottlieb et al. | |
| 2010/0126858 A1 | 5/2010 | Saito et al. | |
| 2012/0046533 A1* | 2/2012 | Voskanyan | A61B 5/14532 |
| | | | 600/347 |
| 2012/0171774 A1 | 7/2012 | Cherian et al. | |
| 2012/0190950 A1* | 7/2012 | Yang | C12Q 1/001 |
| | | | 600/345 |
| 2014/0027312 A1* | 1/2014 | Macfie | G01N 27/3274 |
| | | | 205/792 |
| 2014/0197042 A1 | 7/2014 | Zhang et al. | |
| 2019/0079044 A1* | 3/2019 | Ringemann | G01N 27/327 |

OTHER PUBLICATIONS

Written Opinion for International Application No. PCT/US2018/053068 filed on Sep. 21, 2018 on behalf of California Institute of Technology, dated Jan. 18, 2019. 7 pages.

* cited by examiner

SWITCHABLE LOW VOLTAGE ELECTROCHEMICAL SENSING FOR INTERFERING SPECIES REJECTION

CROSS REFERENCE TO RELATED APPLICATIONS

The present application claims priority to U.S. Provisional Patent Application No. 62/564,921, filed on Sep. 28, 2017, the disclosure of which is incorporated herein by reference in its entirety.

TECHNICAL FIELD

The present disclosure relates to biosensing. More particularly, it relates to switchable low voltage electrochemical sensing for interfering species rejection.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
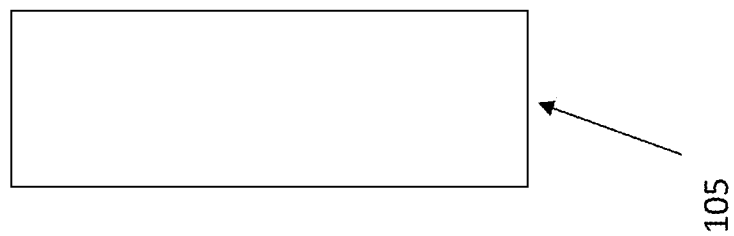
FIG. 1 illustrates a sensor with three electrodes.
Figure 1:
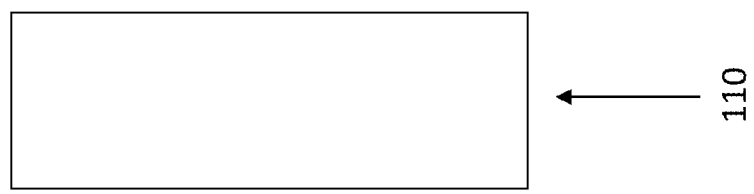
Figure 1:
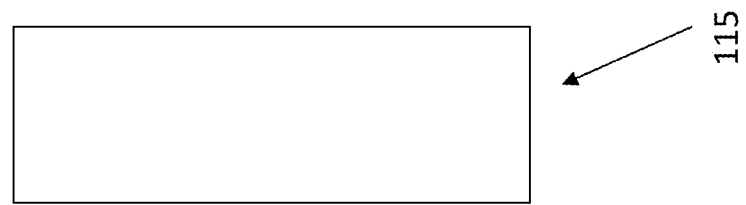

In a first aspect of the disclosure, a sensor to detect a molecule of interest is described, the sensor comprising: a substrate; a working electrode on the substrate; a reference electrode on the substrate; a counter electrode on the substrate; and an enzyme layer covering the working electrode, and optionally the reference electrode and the counter electrode, wherein the sensor is configured to: be implanted in biological tissue; apply a plurality of voltages to the working electrode; measure a plurality of currents at the working electrode, each current of the plurality of currents corresponding to a voltage of the plurality of voltages; generate a measurement curve of the plurality of currents plotted against the plurality of voltages; compare the measurement curve to a reference curve, the reference curve corresponding to a measurement of the molecule of interest without interfering species; if the measurement curve corresponds to the reference curve: select a first current of the plurality of currents corresponding to a first voltage; and calculate a concentration of the molecule of interest based on the first current; if the measurement curve does not correspond to the reference curve: select a second current of the plurality of currents corresponding to a second voltage, the second voltage being lower than the first voltage; and calculate a concentration of the molecule of interest based on the second current.

In a second aspect of the disclosure, a method is described, the method comprising: providing a sensor to detect a molecule of interest, the sensor comprising: a substrate; a working electrode on the substrate; a reference electrode on the substrate; a counter electrode on the substrate; and an enzyme layer covering the working electrode, and optionally the reference electrode and the counter electrode; implanting the sensor in biological tissue; applying a plurality of voltages to the working electrode; measuring a plurality of currents at the working electrode, each current of the plurality of currents corresponding to a voltage of the plurality of voltages; generating a measurement curve of the plurality of currents plotted against the plurality of voltages; comparing the measurement curve to a reference curve, the reference curve corresponding to a measurement of the molecule of interest without interfering species; if the measurement curve corresponds to the reference curve: selecting a first current of the plurality of currents corresponding to a first voltage; and calculating a concentration of the molecule of interest based on the first current; if the measurement curve does not correspond to the reference curve: selecting a second current of the plurality of currents corresponding to a second voltage, the second voltage being lower than the first voltage; and calculating a concentration of the molecule of interest based on the second current.

In a third aspect of the disclosure, a sensor is described, the sensor comprising: a substrate; a working electrode, made of Pt, on the substrate; a reference electrode, made of Pt, on the substrate; a counter electrode, made of Pt, on the substrate; and an enzyme layer, comprising an oxidase enzyme, covering the working electrode, wherein the sensor is configured to: be implanted in biological tissue; apply at least one voltage to the working electrode; measure at least one current at the working electrode; measure a concentration of the molecule of interest based on the at least one current.

DETAILED DESCRIPTION

The present disclosure describes implantable sensors. For a variety of medical conditions, implantable sensors can help patients manage medical conditions. For example, some diabetics use implantable glucose monitors which continuously measure glucose levels, to control their diet and insulin intake. Many of these sensors, including implantable glucose sensors, rely on a coating made with an enzyme, capable of specifically converting a molecule of interest into an electroactive compound, which can generate a current in an appropriately designed electrode. The measured current is typically linearly proportional to the concentration of glucose or of the molecule of interest. Therefore, the concentration can be readily calculated from the current using a scaling factor. Normally, the glucose concentration is reported in a patient-readable format, for example by displaying a value on a display (e.g. a smartphone). However, there are several mechanisms where interfering species in the body can be mistaken for the molecule of interest, thereby generating errors by increasing the current, in turn causing an erroneously high glucose reading to be reported. This interference can be dangerous for a diabetic who can inadvertently overdose on insulin, if given an erroneously high reading.

In other words, other biomolecular or chemical compounds can interfere with the detection process, for example by chemically reacting with the enzyme. For example, the interfering species may reduce the enzyme activity, so that its sensitivity to the molecule of interest is decreased. The interfering species may also, in some cases, react with the enzyme in a similar way as the molecule of interest, generating false positive measurements.

One common source of interference, which the devices of the present disclosure aim to reduce, comprises electroactive compounds which can be present in a patient's system. In most enzymatic sensors, the enzyme itself is typically quite specific. However, these interfering electroactive compounds are small enough to diffuse through, and skip the enzyme layer altogether, thereby directly contributing to the electrode current. Common problematic compounds include acetaminophen (TYLENOL®) and ascorbic acid (vitamin C). Many diabetics, for example, take these medications or supplements to manage associated symptoms of diabetes, therefore their interference is a very common issue for implantable glucose sensors. The levels of many of these interfering species typically varies from day-to-day, so a single point calibration generally cannot cancel out the interfering signal.

In the past, the problem of these electroactive interfering species has been solved by adding extra semi-permeable layers onto the sensor, which can prevent some of these compounds from reaching the electrodes. However, these additional layers present some disadvantages as they generally reduce signal levels, and thus worsen sensor accuracy. The present disclosure presents an innovative method of reducing the effect of interfering species, without the need for an additional blocking layer.

In a traditional sensor, such as a glucose sensor using a glucose oxidase enzyme, an Ag/AgCl reference electrode is typically used. For that type of reference electrode, a measurement voltage of 0.6 V is commonly used. At that measurement voltage, high concentrations, or even typical concentrations, of acetaminophen or ascorbic acid readily cause incorrect glucose measurements. Lower voltages can reduce the sensitivity to interfering species. However, reducing the measurement voltage decreases the signal levels as well, often resulting in minimal benefit.

In the method described in the present disclosure, an innovative three-electrode all-platinum sensor is used. As illustrated in FIG. 1, the setup comprises a platinum working electrode (105), at which the hydrogen peroxide is consumed, a platinum counter electrode (115) that completes the circuit, and a platinum reference electrode (110), with respect to which the potential of the working electrode is maintained. The enzyme coating, typically an oxidase, is coated on the working electrode. In some embodiments, the enzyme is also on the reference and counter electrodes. As known to the person of ordinary skill in the art, the electroactive species generated by oxidases is hydrogen peroxide. The sensor of the present disclosure has better selectivity towards hydrogen peroxide, when compared to most conventional sensors. By using a low voltage measurement with the sensor of the present disclosure, it is possible to reject most common interfering species with an acceptable reduction in sensitivity.

For example, a Pt/Pt/Pt sensor, as described herein, at a measuring voltage of 0.4 V (at the working electrode, with respect to the reference electrode) typically has similar sensitivity to a Pt/AgCl sensor at a measuring voltage of 0.6 V (at the working electrode, with respect to the reference electrode). At the 0.4 V voltage, the Pt/Pt/Pt sensor, when used with glucose oxidase as a glucose sensor, over reports glucose in a patient with normal glucose levels by 15-30% after a maximum strength dose of acetaminophen. This performance is substantially better than traditional sensors such as Pt/AgCl, which commonly over report glucose by 100% or higher at 0.6 V, even with membranes designed to reject interfering compounds. It can be noted that a typical Pt/AgCl sensor will have a similar sensitivity to hydrogen peroxide (and thus glucose, if coated with glucose oxidase) at 0.6 V, as a Pt/Pt/Pt sensor at 0.4 V, when there are no interfering species. Therefore, these are reasonable voltage values at which to compare the two types of sensors.

At a lower measurement voltage of 0.2 V, the Pt/Pt/Pt sensor sees a sensitivity loss of only 20-30%, but high physiological levels of acetaminophen and ascorbic acid add less than 5% error. Therefore, with a measurable, but still acceptable, decrease in sensitivity, it is possible to achieve a low error due to interfering species. The overall ability to detect glucose is increased, due to the great decrease in the error due to interfering species.

Figure 2:
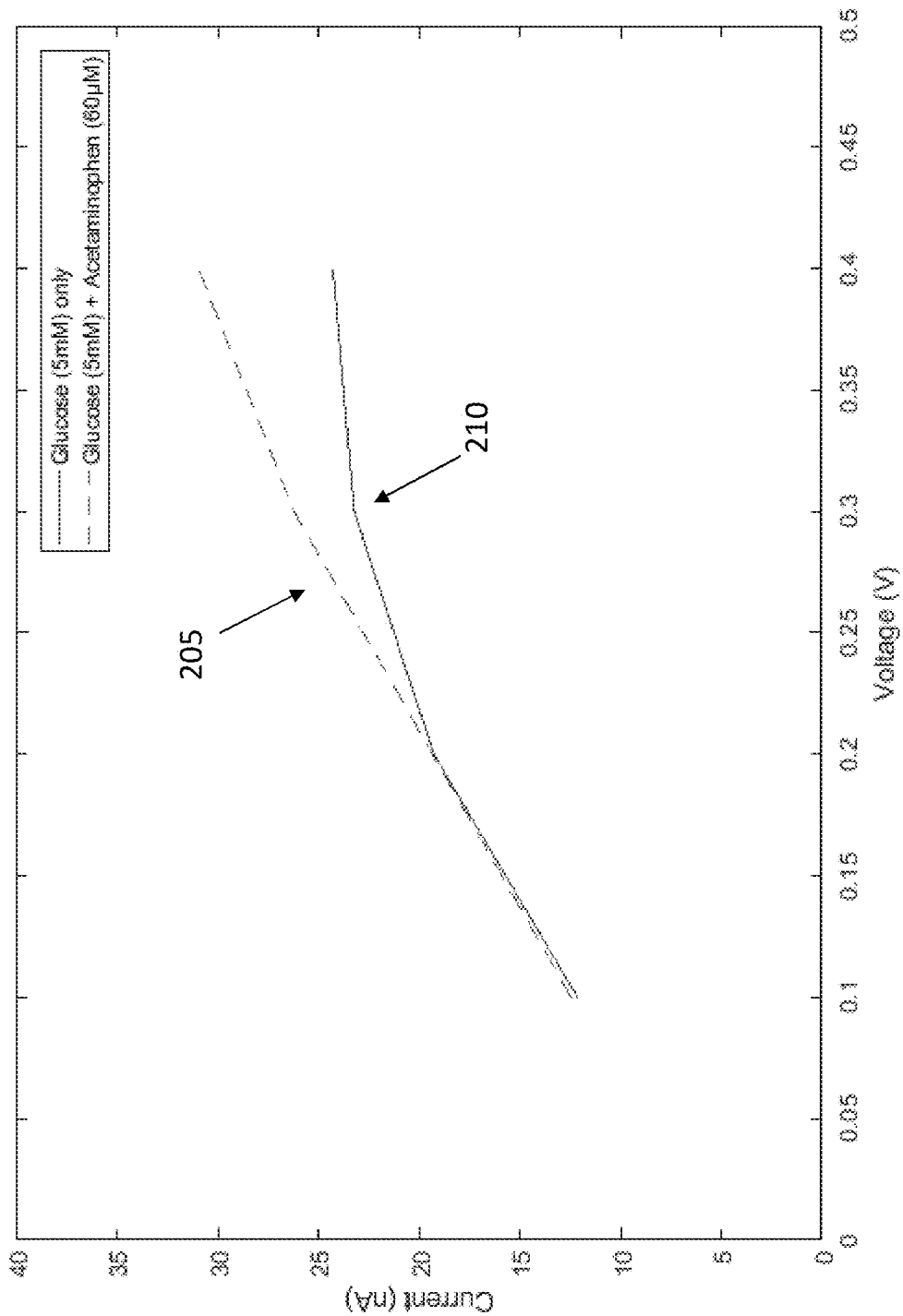
FIG. 2 illustrates voltage vs. current measurements, with and without an acetaminophen interfering species, with an exemplary Pt/Pt/Pt sensor.

FIG. 2 illustrates the current measured from an exemplary Pt/Pt/Pt glucose sensor in the presence of a normal human glucose concentration of 5 mM (210) without interference from high physiological levels of acetaminophen. FIG. 2 also illustrates the current measured from an exemplary Pt/Pt/Pt glucose sensor in the presence of the same, normal human glucose concentration of 5 mM, but with interference from a high physiological level of acetaminophen of 60 µM (205), as a function of different measurement voltages. Therefore, it is possible to take measurements at two or more voltages, for different concentration of glucose with and without interfering species. Once these reference curves or functions are taken, in some embodiments a sensor can take these curves into consideration to determine the concentration of glucose in a new measurement. For example, the sensor may measure the current at two or more voltages, and compare the results to the previously-generated current-voltage plots. Through this comparison, the sensor can determine whether there are interfering species or not, and in turn whether the measurement at higher voltages are more accurate or not. Without interfering species, a measurement at a higher voltage may offer more sensitivity and accuracy, while if there are interfering species, the measurement at a lower voltage may offer more sensitivity and accuracy. Therefore, the sensor can take multiple measurements at multiple voltages, determine which one of these measurements is more accurate, and report a glucose concentration proportional to the measurement determined to be more accurate.

The improved selectivity allows for further improvements to sensitivity in some situations. Because the sensitivity of the electrode to interfering species now varies substantially with higher voltages compared with the sensitivity to hydrogen peroxide, it is possible to determine if there are problematic interfering species present in the patient by looking at sensor currents at various voltages and seeing if the voltage vs. current shape is characteristic of only hydrogen peroxide. In other words, by varying the measurement voltage and observing how the resulting current is affected, it is possible to determine the presence of interfering species.

If no interfering species are present, a high resolution mode (high electrode voltage) can be used. The high voltage measurement would normally be too sensitive to interfering species, and thus negatively affected. However, once it is determined that no interfering species is present, the use of a high voltage will increase the sensitivity of the sensor. If, on the other hand, the variable-voltage analysis determines that interfering species are present, the sensor can switch to a low resolution mode (low electrode voltage), which is less sensitive, or insensitive, to interfering species. For example, the sensor can measure a current vs voltage at different voltages, compare the measurements to a reference curve of the molecule of interest without interfering species, such as (210) for glucose, and determine if interfering species are present or not. If they are not, the sensor can select the current value measured at a higher voltage, where sensitivity to the molecule of interest (e.g. glucose) is higher. The concentration of the molecule of interest is calculated based on the selected current, which has higher sensitivity. If interfering species are present, the sensor can select the current value measured at a lower voltage, where the rejection of interfering compounds (e.g. acetaminophen) is greater. The concentration of the molecule of interest is calculated based on the selected current, which is less sensitive to the presence of interfering compounds.

In some embodiments, the present disclosure describes an implantable electrochemical sensor which comprises three electrodes made of platinum, to selectively measure the concentration of an electroactive compound at low voltages, typically from 0.1 V to 0.3 V. In some embodiments, the electrochemical sensor is coated with an enzyme capable of transducing a small molecule of interest into an electroactive compound. In some embodiments, only the working electrode of the sensor is coated with the enzyme. In some embodiments, the reference and counter electrodes are additionally coated with the enzyme. In some embodiments, the enzyme is an oxidase enzyme, such as glucose oxidase, lactate oxidase, uricase oxidase, urease oxidase or other enzymes from the oxidase family. In some embodiments, the electroactive compound is hydrogen peroxide. In some embodiments, the implantable electrochemical sensor takes measurements at a variety of electrode voltages, and subsequently matches the shape of the acquired reading to a reference reading with no interfering species, to determine the accuracy of the reading as a measure of the species of interest.

In some embodiments, therefore, the sensor can compare the current, measured as a function of the measurement voltage, to one or more reference curves, to determine whether interfering species are present or not. If the interfering species are not present, the sensor sets the measurement voltage to high and carries out the measurement. If the interfering species are present, the sensor sets the measurement voltage to low and carries out the measurement. In some embodiments, the low voltage range lies between 0 and 0.3 V with respect to the Pt reference, and the high voltage range lies between 0.3 V and 0.6 V with respect to the Pt reference. The voltage of 0.3 V can be considered part of the low or high voltage range, depending on the specific setup. In some embodiments, the low voltage range is between 0.0001 and 0.3 V.

In some embodiments, the sensor is configured to apply two or more voltages to the working electrode, and measure each corresponding current at the working electrode. The voltage vs current curves can be compared to reference curves, to determine which of the curves has the greatest sensitivity.

In some embodiments, within the classification of oxidase proteins, the preferred target molecules of interest are those used in human health monitoring applications. For example, other oxidase enzymes that may be used comprise: malate oxidase, EC 1.1.3.3, hexose oxidase, EC 1.1.3.5, aryl-alcohol oxidase, EC 1.1.3.7, L-gulonolactone oxidase, EC 1.1.3.8, pyranose oxidase, EC 1.1.3.10, L-sorbose oxidase, EC 1.1.3.11, pyridoxine 4-oxidase, EC 1.1.3.12, (S)-2-hydroxy-acid oxidase, EC 1.1.3.15, ecdysone oxidase, EC 1.1.3.16, secondary-alcohol oxidase, EC 1.1.3.18, 4-hydroxymandelate oxidase, EC 1.1.3.19, long-chain-alcohol oxidase, EC 1.1.3.20, thiamine oxidase, EC 1.1.3.23, hydroxyphytanate oxidase, EC 1.1.3.27, N-acylhexosamine oxidase, EC 1.1.3.29, polyvinyl-alcohol oxidase, EC 1.1.3.30, D-Arabinono-1,4-lactone oxidase, EC 1.1.3.37, vanillyl-alcohol oxidase, EC 1.1.3.38, D-mannitol oxidase, EC 1.1.3.40, alditol oxidase, EC 1.1.3.41, choline dehydrogenase, EC 1.1.99.1, gluconate 2-dehydrogenase EC 1.1.99.3, glucooligosaccharide oxidase, EC 1.1.99.B3, alcohol dehydrogenase, EC 1.1.99.8, cellobiose dehydrogenase, EC 1.1.99.18, aldehyde oxidase, EC 1.2.3.1, glyoxylate oxidase, EC 1.2.3.5, indole-3-acetaldehyde oxidase, aryl-aldehyde oxidase, EC 1.2.3.9, retinal oxidase, EC 1.2.3.11, abscisic-aldehyde oxidase, EC 1.2.3.14, aldehyde ferredoxin oxidoreductase, EC 1.2.7.5, indolepyruvate ferredoxin oxidoreductase, EC 1.2.7.8, aldehyde dehydrogenase, EC 1.2.99.7, dihydroorotate oxidase, EC 1.3.3.1, acyl-CoA oxidase, EC 1.3.3.6, dihydrouracil oxidase, EC 1.3.3.7, tetrahydroberberine oxidase, EC 1.3.3.8, tryptophan alpha,beta-oxidase, EC 1.3.3.10, L-galactonolactone oxidase, EC 1.3.3.12, acyl-CoA dehydrogenase, EC 1.3.99.3, Isoquinoline-1-oxidoreductase, EC 1.3.99.16, quinaldate 4-oxidoreductase, EC 1.3.99.18, D-aspartate oxidase, EC 1.4.3.1, L-amino-acid oxidase, EC 1.4.3.2, monoamine oxidase, EC 1.4.3.4, pyridoxal 5'-phosphate synthase, EC 1.4.3.5, D-glutamate oxidase, EC 1.4.3.7, ethanolamine oxidase, EC 1.4.3.8; putrescine oxidase, EC 1.4.3.10, cyclohexylamine oxidase, EC 1.4.3.12, protein-lysine 6-oxidase, EC 1.4.3.13, D-glutamate(D-aspartate) oxidase, EC 1.4.3.15, L-lysine 6-oxidase, EC 1.4.3.20, primary-amine oxidase, EC 1.4.3.21, 7-chloro-L-tryptophan oxidase, EC 1.4.3.23, N-methyl-L-amino-acid oxidase, EC 1.5.3.2, non-specific polyamine oxidase, EC 1.5.3.B2, N8-acetylspermidine oxidase (propane-1,3-diamine-forming), EC 1.5.3.B3, N6-methyl-lysine oxidase, EC 1.5.3.4, polyamine oxidase (propane-1,3-diamine-forming), EC 1.5.3.B4, N1-acetylpolyamine oxidase, EC 1.5.3.B5, spermine oxidase, EC 1.5.3.B6, pipecolate oxidase, EC 1.5.3.7, dimethylglycine oxidase, EC 1.5.3.10, polyamine oxidase, EC 1.5.3.11, Dihydrobenzophenanthridine oxidase, EC 1.5.3.12, NAD(P)H oxidase, EC 1.6.3.1, urate oxidase, EC 1.7.3.3; 3-acinitropropanoate oxidase, sulfite oxidase, EC 1.8.3.1, methanethiol oxidase, EC 1.8.3.4; prenylcysteine oxidase, EC 1.8.3.5, L-ascorbate oxidase, EC 1.10.3.3, 3-hydroxyanthranilate oxidase, EC 1.10.3.5, rifamycin-B oxidase, EC 1.10.3.6, superoxide dismutase, EC 1.15.1.1, reticuline oxidase, EC 1.21.3.3, lactate oxidase, L-EC 1.1.3.15, D-amino acid oxidase, EC 1.4.3.3, (S)-6-hydroxynicotine oxidase, EC 1.5.3.5, (R)-6-hydroxynicotine oxidase, EC 1.5.3.6, alcohol oxidase, EC 1.1.3.13, pyruvate oxidase, EC 1.2.3.3, glucose oxidase, EC 1.1.3.4), L-glutamate oxidase, EC 1.4.3.11, acyl coenzyme A oxidase, EC 1.3.3.6, choline Oxidase, EC 1.1.3.17, glutathione sulfhydryl oxidase, EC 1.8.3.3, glycerolphosphate oxidase, EC 1.1.3.21, sarcosine oxidase, EC 1.5.3.1, xanthine oxidase, EC 1.1.3.22, oxalate oxidase, EC 1.2.3.4, co-factor(s)=$Mn^{2+}$; cholesterol oxidase, EC 1.1.3.6, gamma-glutamyl-putrescine oxidase, EC undefined, obtained from *Escherichia coli* K12, capable of oxidizing GABA; GABA oxidase, EC undefined, obtained from: *Penicillium* sp. KAIT-M-117, histamine oxidase (diamine oxidase), EC 1.4.3.22, nucleoside oxidase, EC 1.1.3.39, L-lysine oxidase, EC 1.4.3.14, L-aspartate oxidase, EC 1.4.3.16, glycine oxidase, EC 1.4.3.19, galactose oxidase, EC 1.1.3.9.

In some embodiments, the oxidase enzymes used may be: Lactate oxidase (EC 1.1.3.15), D-amino acid oxidase (EC 1.4.3.3), (S)-6-Hydroxynicotine oxidase (EC 1.5.3.5), (R)-6-Hydroxynicotine oxidase (EC 1.5.3.6), Alcohol oxidase (EC 1.1.3.13), Pyruvate oxidase(EC 1.2.3.3), Glucose oxidase (EC 1.1.3.4), Glutamate oxidase (EC 1.4.3.11), Acyl coenzyme A oxidase (EC 1.3.3.6), Choline oxidase (EC 1.1.3.17), Glutathione Sulfhydryl oxidase (EC 1.8.3.3), Glycerolphosphate oxidase (EC 1.1.3.21), Sarcosine oxidase (EC 1.5.3.1), Xanthine oxidase (EC 1.1.3.22), Oxalate oxidase (EC 1.2.3.4), Cholesterol oxidase (EC 1.1.3.6), Gamma-glutamyl-putrescine oxidase (EC undefined), GABA oxidase (EC undefined), Histamine oxidase (Diamine oxidase, EC 1.4.3.22), Nucleoside oxidase (EC 1.1.3.39), L-Lysine oxidase (EC 1.4.3.14), L-Aspartate oxidase (EC 1.4.3.16), Glycine oxidase (EC 1.4.3.19), and Galactose oxidase (EC 1.1.3.9). GABA is defined as gamma alpha-butyric acid.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A method comprising:
   providing a sensor to detect a molecule of interest, the sensor comprising:
      a substrate;
      a working electrode on the substrate;
      a reference electrode on the substrate;
      a counter electrode on the substrate; and
      an enzyme layer covering the working electrode, and implanting the sensor in biological tissue;
   applying a plurality of voltages to the working electrode;
   measuring a plurality of currents at the working electrode, each current of the plurality of currents corresponding to a voltage of the plurality of voltages, the plurality of currents comprising a first current and a second current, the first current being higher than the second current;
   generating a measurement curve of the plurality of currents plotted against the plurality of voltages;
   comparing the measurement curve to a reference curve, the reference curve corresponding to a measurement of the molecule of interest without interfering species, the reference curve consisting of a graph of positive currents versus positive voltages; and,
   if the measurement curve corresponds to the reference curve:
      selecting the first current of the plurality of currents corresponding to a first voltage; and
      calculating a concentration of the molecule of interest based on the first current but not the second current;
   if the measurement curve does not correspond to the reference curve:
      selecting the second current of the plurality of currents corresponding to a second voltage, the second voltage being lower than the first voltage; and
      calculating a concentration of the molecule of interest based on the second current but not the first current.

2. The method of claim 1, wherein the working electrode, the reference electrode, and the counter electrode are made of Pt.

3. The method of claim 2, wherein the second voltage is between 0 and 0.3 V, and the first voltage is between 0.3 and 0.6 V.

4. The method of claim 3, wherein the enzyme layer comprises an oxidase enzyme.

5. The method of claim 3, wherein the molecule of interest is selected from the group consisting of: glucose, lactate, uricase, and urease.

6. The method of claim 1, wherein the interfering species is acetaminophen or ascorbic acid.

7. The method of claim 1, wherein the enzyme layer additionally covers the reference electrode and the counter electrode.

8. The method of claim 4, wherein the oxidase enzyme is selected from the group consisting of: malate oxidase, EC 1.1.3.3, hexose oxidase, EC 1.1.3.5, aryl-alcohol oxidase, EC 1.1.3.7, L-gulonolactone oxidase, EC 1.1.3.8, pyranose oxidase, EC 1.1.3.10, L-sorbose oxidase, EC 1.1.3.11, pyridoxine 4-oxidase, EC 1.1.3.12, (S)-2-hydroxy-acid oxidase, EC 1.1.3.15, ecdysone oxidase, EC 1.1.3.16, secondary-alcohol oxidase, EC 1.1.3.18, 4-hydroxymandelate oxidase, EC 1.1.3.19, long-chain-alcohol oxidase, EC 1.1.3.20, thiamine oxidase, EC 1.1.3.23, hydroxyphytanate oxidase, EC 1.1.3.27, N-acylhexosamine oxidase, EC 1.1.3.29, polyvinyl-alcohol oxidase, EC 1.1.3.30, D-Arabinono-1,4-lactone oxidase, EC 1.1.3.37, vanillyl-alcohol oxidase, EC 1.1.3.38, D-mannitol oxidase, EC 1.1.3.40, alditol oxidase, EC 1.1.3.41, choline dehydrogenase, EC 1.1.99.1, gluconate 2-dehydrogenase EC 1.1.99.3, glucooligosaccharide oxidase, EC 1.1.99.B3, alcohol dehydrogenase, EC 1.1.99.8, cellobiose dehydrogenase, EC 1.1.99.18, aldehyde oxidase, EC 1.2.3.1, glyoxylate oxidase, EC 1.2.3.5, indole-3-acetaldehyde oxidase, aryl-aldehyde oxidase, EC 1.2.3.9, retinal oxidase, EC 1.2.3.11, abscisic-aldehyde oxidase, EC 1.2.3.14, aldehyde ferredoxin oxidoreductase, EC 1.2.7.5, indolepyruvate ferredoxin oxidoreductase, EC 1.2.7.8, aldehyde dehydrogenase, EC 1.2.99.7, dihydroorotate oxidase, EC 1.3.3.1, acyl-CoA oxidase, EC 1.3.3.6, dihydrouracil oxidase, EC 1.3.3.7, tetrahydroberberine oxidase, EC 1.3.3.8, tryptophan alpha, beta-oxidase, EC 1.3.3.10, L-galactonolactone oxidase, EC 1.3.3.12, acyl-CoA dehydrogenase, EC 1.3.99.3, Isoquinoline-1-oxidoreductase, EC 1.3.99.16, quinaldate 4-oxidoreductase, EC 1.3.99.18, D-aspartate oxidase, EC 1.4.3.1, L-amino-acid oxidase, EC 1.4.3.2, monoamine oxidase, EC 1.4.3.4, pyridoxal 5'-phosphate synthase, EC 1.4.3.5, D-glutamate oxidase, EC 1.4.3.7, ethanolamine oxidase, EC 1.4.3.8; putrescine oxidase, EC 1.4.3.10, cyclohexylamine oxidase, EC 1.4.3.12, protein-lysine 6-oxidase, EC 1.4.3.13, D-glutamate(D-aspartate) oxidase, EC 1.4.3.15, L-lysine 6-oxidase, EC 1.4.3.20, primary-amine oxidase, EC 1.4.3.21, 7-chloro-L-tryptophan oxidase, EC 1.4.3.23, N-methyl-L-amino-acid oxidase, EC 1.5.3.2, non-specific polyamine oxidase, EC 1.5.3.B2, N8-acetylspermidine oxidase (propane-1,3-diamine-forming), EC 1.5.3.B3, N6-methyl-lysine oxidase, EC 1.5.3.4, polyamine oxidase (propane-1,3-diamine-forming), EC 1.5.3.B4, N1-acetylpolyamine oxidase, EC 1.5.3.B5, spermine oxidase, EC 1.5.3.B6, pipecolate oxidase, EC 1.5.3.7, dimethylglycine oxidase, EC 1.5.3.10, polyamine oxidase, EC 1.5.3.11, Dihydrobenzophenanthridine oxidase, EC 1.5.3.12, urate oxidase, EC 1.7.3.3; 3-aci-nitropropanoate oxidase, sulfite oxidase, EC 1.8.3.1, methanethiol oxidase, EC 1.8.3.4; prenylcysteine oxidase, EC 1.8.3.5, L-ascorbate oxidase, EC 1.10.3.3, 3-hydroxyanthranilate oxidase, EC 1.10.3.5, rifamycin-B oxidase, EC 1.10.3.6, superoxide dismutase, EC 1.15.1.1, reticuline oxidase, EC 1.21.3.3, lactate oxidase, L- EC 1.1.3.15, D-amino acid oxidase, EC 1.4.3.3, (S)-6-hydroxynicotine oxidase, EC 1.5.3.5, (R)-6-hydroxynicotine oxidase, EC 1.5.3.6, alcohol oxidase, EC 1.1.3.13, pyruvate oxidase, EC 1.2.3.3, glucose oxidase, EC 1.1.3.4), L-glutamate oxidase, EC 1.4.3.11, acyl coenzyme A oxidase, EC 1.3.3.6, choline Oxidase, EC 1.1.3.17, glutathione sulfhydryl oxidase, EC 1.8.3.3, glycerolphosphate oxidase, EC 1.1.3.21, sarcosine oxidase, EC 1.5.3.1, xanthine oxidase, EC 1.1.3.22, oxalate oxidase, EC 1.2.3.4, co-factor(s)=Mn$^{2+}$; cholesterol oxidase, EC 1.1.3.6, gamma-glutamyl -putrescine oxidase, EC undefined, obtained from *Escherichia coli* K12, capable of oxidizing GABA; GABA oxidase, EC undefined, obtained from: *Penicillium* sp. KAIT-M-117, histamine oxidase (diamine oxidase), EC 1.4.3.22, nucleoside oxidase, EC 1.1.3.39, L-lysine oxidase, EC 1.4.3.14, L-aspartate oxidase, EC 1.4.3.16, glycine oxidase, EC 1.4.3.19, and galactose oxidase, EC 1.1.3.9.

9. The method of claim 4, wherein the oxidase enzyme is selected from the group consisting of: Lactate oxidase (EC 1.1.3.15), D-amino acid oxidase (EC 1.4.3.3), (S)-6-Hydroxynicotine oxidase (EC 1.5.3.5), (R)-6-Hydroxynicotine oxidase (EC 1.5.3.6), Alcohol oxidase (EC 1.1.3.13), Pyruvate oxidase (EC 1.2.3.3), Glucose oxidase (EC 1.1.3.4), Glutamate oxidase (EC 1.4.3.11), Acyl coenzyme A oxidase (EC 1.3.3.6), Choline oxidase (EC 1.1.3.17), Glutathione Sulfhydryl oxidase (EC 1.8.3.3), Glycerolphosphate oxidase (EC 1.1.3.21), Sarcosine oxidase (EC 1.5.3.1), Xanthine oxidase (EC 1.1.3.22), Oxalate oxidase (EC 1.2.3.4), Cholesterol oxidase (EC 1.1.3.6), Gamma-glutamyl-putrescine oxidase (EC undefined), GABA oxidase (EC undefined), Histamine oxidase (Diamine oxidase, EC 1.4.3.22), Nucleoside oxidase (EC 1.1.3.39), L-Lysine oxidase (EC 1.4.3.14), L-Aspartate oxidase (EC 1.4.3.16), Glycine oxidase (EC 1.4.3.19), Urate oxidase, EC 1.7.3.3, and Galactose oxidase (EC 1.1.3.9).

10. The method according to claim 1, wherein each current of the plurality of currents corresponds to a positive voltage of the plurality of voltages and wherein each current of the plurality of currents has only a positive value.

11. The method according to claim 1, wherein the reference curve corresponds to a measurement made at the working electrode and wherein the reference curve comprises a graph of only positive currents versus only positive voltages.

12. A method comprising:
providing a sensor to detect a molecule of interest, the sensor comprising:
a substrate;
a working electrode on the substrate;
a reference electrode on the substrate;
a counter electrode on the substrate; and
an enzyme layer covering the working electrode, the reference electrode, and the counter electrode;
implanting the sensor in biological tissue;
applying a plurality of voltages to the working electrode;
measuring a plurality of currents at the working electrode, each current of the plurality of currents corresponding to a positive voltage of the plurality of voltages, and wherein each current of the plurality of currents has only a positive value, the plurality of currents comprising a first current and a second current, the first current being higher than the second current;
generating a measurement curve of the plurality of currents plotted against the plurality of voltages;
comparing the measurement curve to a reference curve, the reference curve corresponding to a measurement made at the working electrode of the molecule of interest without interfering species, wherein the reference curve comprises a graph of only positive currents versus only positive voltages;
if the measurement curve corresponds to the reference curve:
selecting the first current of the plurality of currents corresponding to a first voltage; and
calculating a concentration of the molecule of interest based on the first current but not the second current;
if the measurement curve does not correspond to the reference curve:
selecting the second current of the plurality of currents corresponding to a second voltage, the second voltage being lower than the first voltage; and
calculating a concentration of the molecule of interest based on the second current but not the first current.

13. The method of claim 12, wherein the working electrode, the reference electrode, and the counter electrode are made of Pt.

14. The method of claim 13, wherein the second voltage is between 0 and 0.3 V, and the first voltage is between 0.3 and 0.6 V.

15. The method of claim 13, wherein the enzyme layer comprises an oxidase enzyme.

16. The method of claim 15, wherein the molecule of interest is selected from the group consisting of: glucose, lactate, uricase, and urease.

17. The method of claim 12, wherein the interfering species is acetaminophen or ascorbic acid.

18. The method of claim 15, wherein the oxidase enzyme is selected from the group consisting of: malate oxidase, EC 1.1.3.3, hexose oxidase, EC 1.1.3.5, aryl-alcohol oxidase, EC 1.1.3.7, L-gulonolactone oxidase, EC 1.1.3.8, pyranose oxidase, EC 1.1.3.10, L-sorbose oxidase, EC 1.1.3.11, pyridoxine 4-oxidase, EC 1.1.3.12, (S)-2-hydroxy-acid oxidase, EC 1.1.3.15, ecdysone oxidase, EC 1.1.3.16, secondary-alcohol oxidase, EC 1.1.3.18, 4-hydroxymandelate oxidase, EC 1.1.3.19, long-chain -alcohol oxidase, EC 1.1.3.20, thiamine oxidase, EC 1.1.3.23, hydroxyphytanate oxidase, EC 1.1.3.27., N-acylhexosamine oxidase, EC 1.1.3.29, polyvinyl-alcohol oxidase , EC 1.1.3.30, D-Arabinono-1,4-lactone oxidase , EC 1.1.3.37, vanillyl-alcohol oxidase, EC 1.1.3.38, D-mannitol oxidase, EC 1.1.3.40, alditol oxidase, EC 1.1.3.41, choline dehydrogenase, EC 1.1.99.1, gluconate 2-dehydrogenase EC 1.1.99.3, glucooligosaccharide oxidase, EC 1.1.99.B3, alcohol dehydrogenase, EC 1.1.99.8, cellobiose dehydrogenase, EC 1.1.99.18, aldehyde oxidase, EC 1.2.3.1, glyoxylate oxidase, EC 1.2.3.5, indole-3-acetaldehyde oxidase, aryl-aldehyde oxidase, EC 1.2.3.9, retinal oxidase, EC 1.2.3.11, abscisic-aldehyde oxidase, EC 1.2.3.14, aldehyde ferredoxin oxidoreductase, EC 1.2.7.5, indolepyruvate ferredoxin oxidoreductase, EC 1.2.7.8, aldehyde dehydrogenase, EC 1.2.99.7, dihydroorotate oxidase, EC 1.3.3.1, acyl-CoA oxidase, EC 1.3.3.6, dihydrouracil oxidase, EC 1.3.3.7, tetrahydroberberine oxidase, EC 1.3.3.8, tryptophan alpha,beta-oxidase, EC 1.3.3.10, L-galactonolactone oxidase, EC 1.3.3.12, acyl-CoA dehydrogenase, EC 1.3.99.3, Isoquinoline-1-oxidoreductase, EC 1.3.99.16, quinaldate 4-oxidoreductase, EC 1.3.99.18, D-aspartate oxidase, EC 1.4.3.1, L-amino-acid oxidase, EC 1.4.3.2, monoamine oxidase, EC 1.4.3.4, pyridoxal 5'-phosphate synthase, EC 1.4.3.5, D-glutamate oxidase, EC 1.4.3.7, ethanolamine oxidase, EC 1.4.3.8; putrescine oxidase, EC 1.4.3.10, cyclohexylamine oxidase, EC 1.4.3.12, protein-lysine 6-oxidase, EC 1.4.3.13, D-glutamate(D-aspartate) oxidase, EC 1.4.3.15, L-lysine 6-oxidase, EC 1.4.3.20, primary-amine oxidase, EC 1.4.3.21, 7-chloro-L-tryptophan oxidase, EC 1.4.3.23, N-methyl-L-amino-acid oxidase, EC 1.5.3.2, non-specific polyamine oxidase, EC 1.5.3.B2, N8-acetylspermidine oxidase (propane-1,3-diamine-forming), EC 1.5.3.B3, N6-methyl-lysine oxidase, EC 1.5.3.4, polyamine oxidase (propane-1,3-diamine-forming), EC 1.5.3.B4, N1-acetylpolyamine oxidase, EC 1.5.3.B5, spermine oxidase, EC 1.5.3.B6, pipecolate oxidase, EC 1.5.3.7, dimethylglycine oxidase, EC 1.5.3.10, polyamine oxidase, EC 1.5.3.11, Dihydrobenzophenanthridine oxidase, EC 1.5.3.12, urate oxidase, EC 1.7.3.3; 3-aci -nitropropanoate oxidase, sulfite oxidase, EC 1.8.3.1, methanethiol oxidase, EC 1.8.3.4; prenylcysteine oxidase, EC 1.8.3.5, L-ascorbate oxidase, EC 1.10.3.3, 3-hydroxyanthranilate oxidase, EC 1.10.3.5, rifamycin-B oxidase, EC 1.10.3.6, superoxide dismutase, EC 1.15.1.1, reticuline oxidase, EC 1.21.3.3, lactate oxidase, L- EC 1.1.3.15, D-amino acid oxidase, EC 1.4.3.3, (S)-6-hydroxynicotine oxidase, EC 1.5.3.5, (R)-6-hydroxynicotine oxidase, EC 1.5.3.6, alcohol oxidase, EC 1.1.3.13, pyruvate oxidase, EC 1.2.3.3, glucose oxidase, EC 1.1.3.4), L-glutamate oxidase, EC 1.4.3.11, acyl coenzyme A oxidase, EC 1.3.3.6, choline Oxidase, EC 1.1.3.17, glutathione sulfhydryl oxidase, EC 1.8.3.3, glycerolphosphate oxidase, EC 1.1.3.21, sarcosine oxidase, EC 1.5.3.1, xanthine oxidase, EC 1.1.3.22, oxalate oxidase, EC 1.2.3.4, co-factor(s)=$Mn^{2+}$; cholesterol oxidase, EC 1.1.3.6, gamma-glutamyl -putrescine oxidase, EC undefined, obtained from *Escherichia coli* K12, capable of oxidizing GABA; GABA oxidase, EC undefined, obtained from: *Penicillium* sp. KAIT -M-117, histamine oxidase (diamine oxidase), EC 1.4.3.22, nucleoside oxidase, EC 1.1.3.39, L-lysine oxidase, EC 1.4.3.14, L-aspartate oxidase, EC 1.4.3.16, glycine oxidase, EC 1.4.3.19, and galactose oxidase, EC 1.1.3.9.

19. The method of claim 15, wherein the oxidase enzyme is selected from the group consisting of: Lactate oxidase (EC 1.1.3.15), D-amino acid oxidase (EC 1.4.3.3), (S)-6-Hydroxynicotine oxidase (EC 1.5.3.5), (R)-6-Hydroxynicotine oxidase (EC 1.5.3.6), Alcohol oxidase (EC 1.1.3.13), Pyruvate oxidase(EC 1.2.3.3), Glucose oxidase (EC 1.1.3.4), Glutamate oxidase (EC 1.4.3.11), Acyl coenzyme A oxidase (EC 1.3.3.6), Choline oxidase (EC 1.1.3.17), Glutathione Sulfhydryl oxidase (EC 1.8.3.3), Glycerolphosphate oxidase (EC 1.1.3.21), Sarcosine oxidase (EC 1.5.3.1), Xanthine oxidase (EC 1.1.3.22), Oxalate oxidase (EC 1.2.3.4), Cholesterol oxidase (EC 1.1.3.6), Gamma-glutamyl-putrescine oxidase (EC undefined), GABA oxidase (EC undefined), Histamine oxidase (Diamine oxidase, EC 1.4.3.22), Nucleoside oxidase (EC 1.1.3.39), L-Lysine oxidase (EC 1.4.3.14), L-Aspartate oxidase (EC 1.4.3.16), Glycine oxidase (EC 1.4.3.19), Urate oxidase, EC 1.7.3.3, and Galactose oxidase (EC 1.1.3.9).

* * * * *